United States Patent [19]

Tolman et al.

[11] 4,093,714
[45] June 6, 1978

[54] 9β-D-ARABINOFURANOSYLPURINE NUCLEOTIDES AND METHOD OF USE

[75] Inventors: Richard L. Tolman, Berkley Heights, N.J.; Robert W. Sidwell, Irvine; Ganapathi R. Revankar, Santa Ana, both of Calif.

[73] Assignee: ICN Pharmaceuticals, Inc., Irvine, Calif.

[21] Appl. No.: 451,639

[22] Filed: Mar. 15, 1974

Related U.S. Application Data

[63] Continuation-in-part of Ser. No. 342,617, Mar. 19, 1975, abandoned.

[51] Int. Cl.$^2$ .................. A61K 31/52; C07H 19/20; A61K 31/70
[52] U.S. Cl. .................................. 424/180; 536/27; 536/28; 536/29
[58] Field of Search .................. 260/211.5 R; 536/27, 536/28, 29

[56] References Cited

U.S. PATENT DOCUMENTS

| | | | |
|---|---|---|---|
| 3,049,536 | 8/1962 | Reiff et al. | 260/211.5 R |
| 3,170,917 | 2/1965 | Laufer et al. | 260/211.5 R |
| 3,300,478 | 1/1967 | Wechter | 260/211.5 R |
| 3,314,938 | 4/1967 | Kawashima et al. | 260/211.5 R |
| 3,317,512 | 5/1967 | Wechter | 260/211.5 R |
| 3,328,389 | 6/1967 | Shimizu et al. | 260/211.5 R |
| 3,337,530 | 8/1967 | Hanze | 260/211.5 R |
| 3,728,329 | 4/1973 | Yano et al. | 260/211.5 R |
| 3,755,296 | 8/1973 | Kanai et al. | 260/211.5 R |

Primary Examiner—Johnnie R. Brown
Attorney, Agent, or Firm—K. H. Boswell

[57] ABSTRACT

9-β-D-Arabinofuranosyl nucleotides of the following structure are disclosed:

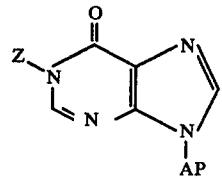

wherein AP is a 3' or 5' phosphorylated arabinofuranoside or the corresponding 3', 5' cyclic phosphate joined by a glycoside linkage to $N^9$ of the aglycon component of said nucleotide, and Z is H, $C_1$–$C_6$ alkyl, $C_7$–$C_{10}$ aralkoxy, or hydroxy.

Compounds prepared according to the invention exhibit antiviral activity in vitro, while others are precursors useful in the synthesis of bioactive compounds.

14 Claims, No Drawings

9β-D-ARABINOFURANOSYLPURINE NUCLEOTIDES AND METHOD OF USE

CROSS REFERENCE TO RELATED APPLICATIONS

This application is a continuation-in-part of our co-pending application entitled, 9-β-D-ARABINOFURANOSYLHYPOXANTHINE-5'-PHOSPHATE, Ser. No. 342,617, filed Mar. 19, 1973 now abandoned and assigned to the same assignee as this application.

BACKGROUND OF THE INVENTION

During the past decade, many nucleoside analogs have been found to exhibit good antitumor and antiviral activities. Among the presently known synthetic nucleosidic antiviral agents, the more important are generally considered to be 5'-iodo-2'-deoxyuridine (IDU); 9-β-D-arabinofuranosyladenine (Ara-A); and 1-β-D-arabinofuranosylcytosine (Ara-C). Of these compounds, only IDU is commercially available specifically as an antiviral agent, and this compound has extremely low solubility, i.e., a maximum solubility of about 0.1 weight percent, and is also highly toxic. Ara-A presently is undergoing clinical testing as an antiviral agent, and while the reported evidence suggests that Ara-A is an effective agent against a spectrum of virus infections, its utility is severely limited by its low solubility, and by human toxic symptoms which include mild nausea, transient leukopenia and central nervous system involvement which causes illusions and hallucinations.

When nucleosidic analogs are used to inhibit viral growth, the nucleosides are usually metabolized in vivo to their corresponding mono or poly phosphates which are the actual inhibitors of such growth. A major obstacle in the use of nucleoside analogs in chemotherapy has been the emergence of cellular resistance whereby such compounds are degraded to a form where they may be less effective inhibitors. It is accordingly desirable to have nucleosidic analogs which are capable of effectively inhibiting the development of virus infections and which also possess superior solubility and less toxicity than presently known antiviral agents. The production of such a compound, however, is quite difficult, since relatively few nucleosidic compounds are known which have demonstrated antiviral activity, even in vitro. Moreover, to provide such a compound which has acceptable activity and which is also capable of contacting the virus infection in effective concentrations makes this task exceedingly difficult.

In German Patent Application No. 2,047,368, 9-β-D-arabinofuranosyladenine-5'-phosphate is suggested as a compound useful as an antiviral agent. This compound, however, as an AMP analog and a precursor to an ATP analog is rapidly degraded in the metabolic system (eventually to uric acid). Since ATP levels in the metabolic system are carefully maintained by the metabolic system at low levels the effectiveness of such compounds as antiviral agents is accordingly diminished.

In view of the foregoing, we thus sought to prepare additional nucleosidic analogs in order to investigate the possibilities that certain such compounds might be capable of withstanding rapid metabolic degradation and also penetrating the cellular membrane and contacting virus infections in effective concentrations. As will be apparent from the description which follows, we have synthesized 9-β-D-arabinofuranosylhypoxanthine-5'-phosphate and found such compound to demonstrate marked activity against a spectrum of herpes and other DNA viruses. We have also synthesized other 9-β-D-arabinofuranosyl nucleotides having a phosphorylated arabinoside joined thereto by a glycoside linkage and found that many of them demonstrate marked activity against a spectrum of herpes and other DNA viruses.

SUMMARY OF THE INVENTION

The present invention thus relates to compounds which are useful as antiviral agents and have the following structure:

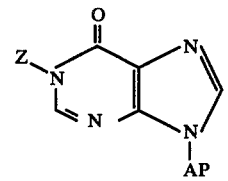

wherein Z is H, $C_1$–$C_6$ alkyl, $C_7$–$C_{10}$ aralkoxy, or hydroxy, and AP is a 5' or 3' phosphorylated arabinofuranoside or the corresponding 3', 5' cyclic phosphate joined by a glycoside linkage to $N^9$ of the aglycon component of the 9-β-D-arabinofuranosyl nucleotide.

The phosphorylated arabinofuranoside moiety, AP, of the 9-β-D-arabinofuranosyl purine nucleotides of the invention, when phosphorylated at the 5' position, has the general structure:

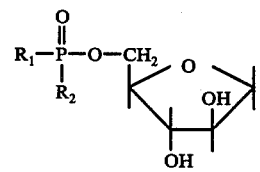

wherein $R_1$ is OH, —O—$C_1C_6$ alkyl or OM and $R_2$ is OH or OM, with M normally being ammonium, substituted ammonium such as triethyl ammonium, or an alkali metal or alkaline or alkaline earth metal, or other metal which forms a physiologically acceptable compound.

When AP is phosphorylated in the 3' position, $R_1$ and $R_2$ are the same as described above for the 5' position.

When AP is 3', 5' cyclic phosphate, the phosphate moiety is linked to the sugar base at the 3' OH position and $R_1$ is as described above.

DETAILED DESCRIPTION OF THE INVENTION

The 9-β-D-arabinofuranosyl purine nucleotides of this invention may be prepared by the methods set forth in Examples I - XI which follow.

9-β-D-Arabinofuranosyladenine nucleotides may be prepared by first reacting the appropriate furanosyl-nucleoside with a suitable phosphorus oxychloride compound, as, for example, phosphorus oxychloride or its methyl ester, phosphorodichloridate, in a suitable trialkylphosphate solvent, preferably trimethylphosphate, to form the corresponding furanosyl nucleotide. The nucleoside is added to the phosphorus oxychloride compound solution with stirring and the reaction allowed to proceed to completion at from about 0° to about 15° which time is from about 3 hours to about 24 hours. The nucleotide product of the first step is next treated with an alkaline carbonate, as for example sodium bicarbonate or potassium bicarbonate until a stable pH of from about 5 to about 7 is achieved. The adenine nucleotide is then recovered as, for example, by chromatography and lyophilization.

9-β-D-Arabinofuranosylhypoxanthine nucleotides may also be prepared by reacting the appropriate adenine nucleotide in water with glacial acetic acid and sodium nitrite. The sodium nitrite is preferably added to a solution of the nucleotide and glacial acetic acid and the reaction is allowed to proceed to completion at from about 10° to about 30° and preferably 20° to 25°. The reaction period may be from about 15 hours to about 24 hours. The nucleotide product is recovered and neutralized with an alkaline carbonate as, for example, potassium bicarbonate or sodium bicarbonate and recovered as by crystallization.

In the following examples, ultra-violet spectra were recorded on a Cary-15 spectrophotometer and infrared spectra were determined on a Perkin-Elmer Model 257 spectrophotometer. All temperatures are in degrees centigrade and all parts by weight unless otherwise specified.

EXAMPLE I

9-β-D-Arabinofuranosylhpyoxanthine-5'-phosphate - Method 1

To an ice cooled suspension of 9-βD-arabinofuranosyladenine-5'-monophosphate (ara-AMP) (2.0 g) in water (15 ml) and glacial acetic acid (3.0 ml) was added sodium nitrite (2.5 g). The flask was loosely stoppered and stirred for 2–3 hours in the ice bath. The stirring was continued overnight (15–16 hours), without adding ice to the ice bath. Tlc (silica gel, solvent $L_2$: IPA/NH$_4$OH/H$_2$O; 55/10/35, v/v) indicated completion of the reaction. The clear, colorless solution was evaporated in vacuo to dryness, the residue was dissolved in water (20 ml), and was carefully neutralized with solid KHCO$_3$. The neutral solution was applied to a column containing 75 ml of Dowex 50[H$^+$] ion exchange resin. The column was washed with water and the fractions containing uv-absorbing material were pooled and concentrated in vacuo to about 25 ml. Ethanol (50 ml) was added to the concentrated solution and chilled overnight. The solid that separated was collected, washed with cold water and crystallized from water as colorless needles.

m.p. −198°–199° (dec.); $[\alpha]_D^{25}$ + 9.8 (c = 1, water) yield - 1.60 g (79.8%)

Anal. calcd for C$_{10}$H$_{13}$N$_4$O$_8$P (348.2): C, 34.48; H, 3.74; N, 16.10. Found: C, 34.45; H, 3.80; N, 15.89.

Uv: $\lambda_{max}^{pH\ 1}$ 249 mμ (E 12,700) $\lambda_{max}^{pH\ 7}$ 248 mμ (E 13,600) $\lambda_{max}^{pH\ 11}$ 252 mμ (E 14,400).

EXAMPLE II

9-β-D-Arabinofuranosylhypoxanthine-5'-phosphate - Method 2

Ara-I (9-β-D-arabinofuranosyl-hypoxanthine) was added with stirring to a precooled (~5°, ice bath) mixture of 100 ml trimethyl phosphate and 12.3 g phosphorus oxychloride. After all the solid had dissolved (~5 min), it was stored for 4 hours at 0°. Tlc (silica gel, solvent IPA/NH$_4$OH/H$_2$O; 55/10/35) indicated the reaction to be complete, and it was poured slowly into ice water containing 26.3 g NaHCO$_3$. The ice water solution was allowed to stand for 1 hour to stabilize the pH at 6. The solution was extracted with ether (3 × 75 ml) to remove the trimethylphosphate. The volume of the aqueous phase was reduced in vacuo until crystals (salt) began to form. Water was added to dissolve the crystals, and the solution was applied to the top of a 750 g Barneby Cheney charcoal column. The charcoal was washed with water to remove salts, and then the product was eluted off with 50% aqueous MeOH containing 10% NH$_4$OH. The eluant was reduced to a small volume in vacuo (ammonia odor was gone), and the pH was adjusted to 2. EtOH was added until the solution became turbid and the solution was stored at 5°. Crystals were filtered and dried at 40° under aspirator vacuum (1st crop-5.5 g); nmr (DMSO-d$_6$), σ8.1, 8.19 (2H, s, H-2, H-8) 6.28 (1H, m, H-1').

EXAMPLE III

9β-D-Arabinofuranosyladenine-5'-O-methylphosphate

Methyl phosphorodichloridate (10.0 g, 0.067 mole) in freshly distilled trimethyl phosphate (100.0 ml, 0.71 mole) was cooled to 0°–5° in an ice bath. The ice bath was removed as 9-β-D-arabinofuranosyladenine (10.0 g, 0.037 mole, dried at 80° for 5 hrs) was added. There was no noticeable initial rise in temperature. The temperature was monitored between 5°–20°. After 2 hours a clear solution was obtained, which was stored overnight at 4°. The solution was then poured onto ice water (400.0 ml) containing 6.0 g of sodium bicarbonate. Additional sodium bicarbonate was added periodically until the pH was stable at 5–6, about an hour. Trimethyl phosphate was removed by extraction with ether (4 × 150 ml). Dissolved ether and excess water were removed by evaporation under reduced pressure until salts began to crystallize. Enough water was added to achieve solution and the pH was checked (6–7). The solution was added carefully to the top of a Dowex 1 × 2 column (formate form, 100–200 mesh, 300 ml). The column was washed with water until no further ultraviolet absorbing species were detected in the eluant. Gradient elution (water to 0.1M formic acid) gave the product in a thick band. The appropriate fractions were evaporated in vacuo, keeping the temperature below 30°, to about 100 ml. The remaining solution was frozen and lyophilized to obtain white, fluffy solid weighing 6.50 g (48.0%), m.p. 170°–190° (dec.); $[\alpha]_D^{25}$ + 48.7° (c. 1.0, water); uv, $\lambda_{max}^{pH\ 1}$ 257 nm (ε 14,200): $\lambda_{max}^{pH\ 7}$ 258 nm (ε 13,000); $\lambda_{max}^{pH}$ 258 nm(ε 13,000).

Anal. calcd for C$_{11}$H$_{16}$N$_5$O$_7$P (361.25); C, 36.57; H, 4.47; N, 19.39. Found: C, 36.42; H, 4.26; N, 19.19.

EXAMPLE IV

9-β-D-Arabinofuranosylhypoxanthine-5'-O-methylphosphate

To an ice cooled solution of 9-β-D-arabinofuranosyladenine-5'-O-methylphosphate (2.0 g, 0.0055 mole) (prepared by the method of Example III) in water (15.0 ml) and glacial acetic acid (3.0 ml) was added sodium nitrite (2.25 g, 0.032 mole). The flask was loosely stoppered and stirred for 2–3 hours in an ice bath. The stirring was continued overnight (15–16 hrs) without adding ice to the ice bath. Tlc (silica gel, solvent IPA/NH$_4$OH/H$_2$O; 55/10/35; v/v) indicated the completion of the reaction. The clear, colorless solution was evaporated in vacuo to dryness. The residue was dissolved in water (10 ml), and carefully neutralized with solid potassium bicarbonate. The neutral solution was applied to a column containing 80 ml of Dowex 50

× 8 (H⁺) ion exchange resin. The column was washed with water and the fractions containings uv-absorbing material were pooled and concentrated in vacuo to about 20 ml. Ethanol (50 ml) was added to the concentrated aqueous solution and it was chilled overnight. The solid that separated was collected, washed with a small volume of cold water and crystallized from aqueous ethanol to yield 1.65 g (82.3%), m.p. 160°–180° (dec.); $[\alpha]_D^{25} + 55.7°$ (c 1.0, water); uv, $\lambda_{max}^{pH\,1}$ 248 nm ($\epsilon$ 10,300); $\lambda_{max}^{pH\,7}$ 248 nm ($\epsilon$ 9,900); $\lambda_{max}^{pH\,11}$ 251 nm ($\epsilon$ 12,000).

Anal. calcd for $C_{11}H_{15}N_4O_8P$ (362.23); C, 36.48; H, 4.17; N, 15.46. Found: C, 36.22; H, 4.39; N, 15.49.

EXAMPLE V

9-β-D-Arabinofuranosyl-N¹-hydroxyhypoxanthine-5′-phosphate

To an ice cooled suspension of 9-β-D-arabinofuranosyladenine-N¹-oxide-5′-phosphate (prepared as in commonly assigned, copending application to R. Sidwell et al, 9-β-D-arabinofuranosyladenine-5′-phosphates, Serial Number 383,661, now Patent No. 3,831,424 the disclosure of which is incorporated herein by reference) (2.0 g, 0.0055 mole) in water (15 ml) containing glacial acetic acid (3.0 ml) was added sodium nitrite (2.5 g, 0.036 mole). The flask was loosely stoppered and stirred for 2–3 hours in an ice bath. The reaction was allowed to proceed for a further 15 hours. After evaporation of the clear reaction mixture and neutralization with potassium bicarbonate, it was treated in the same way as described in Example IV to yield 1.35 g (67.3%), m.p. > 150° (dec.); uv, $\lambda_{max}^{pH\,1}$ 251 nm ($\epsilon$ 11,650); $\lambda_{max}^{pH\,7}$ 255 nm ($\epsilon$ 11,650); $\lambda_{max}^{pH\,11}$ 255 nm ($\epsilon$ 12,000).

Anal. calcd for $C_{10}H_{13}N_4O_9P$ (364.20): C, 32,98; H, 3.59; N, 15.38. Found: C, 32.82; H, 3.62; N, 15.19.

EXAMPLE VI

9-β-D-Arabinofuranosyl-N¹-benzyloxyhypoxanthine-5′-phosphate

A solution of 9-β-D-arabinofuranosyl-N¹-hydroxyhypoxanthine-5′-phosphate (1.12 g, 0.0030 mole) in dry DMSO (10 ml) was treated with 1,5-diazabicyclo [5,4,0] undec-5-ene (DBU, 0.5 g) and stirred at room temperature. The gelatinous precipitate which initially formed dissolved after 30 min with rapid stirring. The mixture was treated with benzyl bromide (0.65 g, 0.0038 mole) and stirring was continued at room temperature overnight. Tlc (silica gel solvent IPA/NH₄OH/H₂O; 55/10/35, v/v) indicated the completion of the reaction. The reaction mixture was then poured into a cold (0°–5°) ethanol-ether mixture (1:1, 500 ml). The mixture was filtered and the white residue was washed thoroughly wih anhydrous either (5 × 50 ml). The hygroscopic solid was dissolved in a minimum volume of water and cautious addition of ethanol caused the product to precipitate as white crystals. The mixture was chilled overnight and the product was collected, washed with ethanol and dried to yield 0.80 g (57.4%), m.p. > 165° (dec.); uv, $\lambda_{max}^{pH\,1}$ 250 nm ($\epsilon$ 13,600); $\lambda_{max}^{pH\,7}$ 255 nm ($\epsilon$ 14,500); $\lambda_{max}^{pH\,11}$ 255 nm ($\epsilon$ 14,500).

Anal. calcd for $C_{17}H_{19}N_4P$ (454.33); C, 44.91; H, 4.21; N, 12.33. Found: C, 45.18; H, 4.43; N, 12.61.

EXAMPLE VII

9-β-D-Arabinofuranosyl-N¹-methylhyproxanthine-5′-phosphate

9-β-D-Arabinofuranosylhypoxanthine-5′-phosphate (3.0 g, 0.0086 mole) was dissolved in dry pyridine (90 ml) containing triethylamine (2.25 g) and acetic anhydride (5.7 g) and the solution was stirred at room temperature for 3 hours. The pale yellow solution was evaporated in vacuo and the oily residue was mixed with about 50 g of ice. It was again evaporated to dryness. This process was repeated thrice with 25 g portions of ice. The residue was taken in 100 ml of water and extracted with ether. The clear aqueous solution was frozen and lyophilized to obtain 5.0 g of syrupy 9-(2,3-di-O-acetyl-β-D-arabinofuranosyl) hypoxanthine-5′-phosphate triethylammonium salt.

The triethylammonium salt (2.5 g) was dissolved in anhydrous DMSO(50 ml) and sodium hydride (350 g, 57% oil dispersion) was added to it. The mixture was stirred at room temperature with the exclusion of moisture for 2 hours. The clear mixture was treated with methyl iodide (5.0 ml) and the stirring continued for 4 hours. The brown mixture was then poured into a cold ethanol-ether mixture [600 ml (1:3)] and chilled overnight. The mixture was filtered, the residue dissolved in a small volume of water and applied to a Dowex 1 × 2 column (formate form, 100–200 mesh, 75 ml). The product was eluted with water and the appropriate fractions were evaporated in vacuo to give a colorless syrup (2.0 g). It was deacetylated with methanolic ammonia (50 ml, saturated at 0°) at room temperature for 15 hours. The white solid was collected, dissolved in water (10 ml) and passed through a Dowex 50 × 8 (H⁺) column (25 ml). The eluate was concentrated in vacuo to about 5 ml and ethanol was added. The precipitate that separated after chilling, was collected and crystallized from aqueous ethanol to yield 0.30 g, m.p. > 125° (dec.); uv, $\lambda_{max}^{pH\,1}$ 253 nm ($\epsilon$ 7,900); $\lambda_{max}^{pH\,7}$ 261 nm ($\epsilon$ 7,200); $\lambda_{max}^{pH\,11}$ 261 nm ($\epsilon$ 7,200).

Anal. calcd for $C_{11}H_{15}N_4O_8P$ (362.23); C, 36.48; H, 4.17; N, 15.47. Found: C, 36.28; H, 4.36; N, 15.32.

EXAMPLE VIII

9-β-D-Arabinofuranosyl-N¹-methylhypoxanthine-5′-O-methylphosphate

A solution of 9-β-D-arabinofuranosylhypoxanthine-5′-phosphate (1.0 g, 0.0028 mole) in dry DMSO (10 ml) was treated with 1,5-diazabicyclo[5,4,0]undec-5-ene (0.5 g) followed by methyl iodide (2.0 ml). The reaction was allowed to proceed for 15 hours at room temperature and treated in the same way as described in Example VI to yield 0.40 g (37.0%), m.p. 162°–5° (dec.); uv, $\lambda_{max}^{pH\,1}$ 253 nm ($\epsilon$ 10,050); $\lambda_{max}^{pH\,7}$ 253 nm ($\epsilon$9.500); $\lambda_{max}^{pH\,11}$ 265 nm ($\epsilon$7,450).

Anal. calcd for $C_{12}H_{17}N_4O_8P$ (376.26): C, 38.31; H, 4.55; N, 14.89. Found: C, 38.14; H, 4.68; N, 14.65.

EXAMPLE IX

9-β-D-Arabinofuranosylhypoxanthine-3′,5′-cyclic phosphate

To an ice cooled suspension of 9-β-D-arabinofuranosyladenine-3′,5′-cyclic phosphate (prepared according to the method described in T. Khwaja et al, Docket 135/47, *Cyclic Monophosphates of Nucleosides*, Ser. No. 169,059, filed: Aug. 4, 1971, now U.S.

Pat. No. 3,849,397) (2.0 g, 0.0060 mole) in water (15 ml) containing glacial acetic acid (3.0 ml) was added sodium nitrite (2.5 g, 0.036 mole). The flask was loosely stoppered and stirred for 2–3 hours in an ice bath. The reaction was allowed to proceed 20 hours. After evaporation and neutralization with potassium bicarbonate, it was treated in the same way as described in Example IV to yield, 1.80 g (89.7%), m.p. 240° (dec.), $[\alpha]_D^{25} -49.5°$ (c 1.0, water); uv, $\lambda_{max}^{pH\,1}$ 247 nm ($\epsilon$ 12,100); $\lambda_{max}^{pH\,7}$ 247 nm ($\epsilon$12,400); $\lambda_{max}^{pH\,11}$ 251 nm ($\epsilon$ 13,000).

Anal. calcd. for $C_{10}H_{11}N_4O_7P$ (330.19); C, 36.40; H, 3.35; N, 16.97. Found: C, 36.35; H, 3.39; N, 16.87.

EXAMPLE X

9-$\beta$-D-Arabinofuranosyladenine-3'-phosphate

A mixture of phosphorus oxychloride (1.5 g) and freshly distilled trimethyl phosphate (20.0 ml) was cooled to 0°–5° in an ice bath. The ice bath was removed as finely powdered 5'-O-benzoyl-9-$\beta$-D-arabinofuranosyladenine (1.5 g, 0.0040 mole, dried at 80° overnight) (prepared according to the method of H. Renis et al, *J. Med. Chem.*, 16, 754, [1973]) was added. The temperature was monitored between 5°–15°. After 30 min a clear, colorless solution was obtained, which was stored overnight at 4°. The reaction mixture was then poured onto ice water (100 ml) containing 2.0 g of sodium bicarbonate. Additional sodium bicarbonate was added periodically until the pH was stable at 5–6, (about an hour). Trimethylphosphate was removed by extraction with ether (4 × 75 ml). Dissolved ether and excess of water was removed by evaporation in vacuo until salts began to separate. Enough water was added to achieve solution and the pH was checked (6–7) before placing the solution on the top of a Dowex 1 × 2 column (formate form, 100–200 mesh, 60 ml). The column was washed with water until no ultra-violet absorbing material was present in the eluant. Gradient elution (water to 0.5 M formic acid) and lyophilization of the appropriate fractions yield 0.4 g (24.7%) of a mixture of 2'- and 3'-phosphates.

The above mixture of phosphates (350 mg) was dissolved in freshly prepared 0.01M sodium methoxide in methanol (25 ml) and the solution was allowed to stand at room temperature overnight. The reaction mixture was carefully neutralized with Dowex 50 × 8 (H$^+$). The resin was removed and the filtrate concentrated to about 5 ml. It was applied to a Dowex 1 × 2 column (formate form, 40 ml). The column was washed with water until no ultra-violet absorbing material was present in the eluant. Upon gradient elution (water to 0.5M formic acid), 9-$\beta$-D-arabinofuranosyladenine-2'-phosphate emerged first followed by the 3'-phosphate isomer. The 3'-phosphate fractions were lyophilized to yield 105 mg (10%) of 9-$\beta$-D-arabinofuranosyladenine-3'-phosphate; m.p. 180°–182° (dec.); uv, $\lambda_{max}^{pH\,1}$ 257 nm ($\epsilon$ 6,600); $\lambda_{max}^{pH\,7}$ 258 nm ($\epsilon$6,900); $\lambda_{max}^{pH\,11}$ 258 nm ($\epsilon$ 6,900).

EXAMPLE XI

9-$\beta$-D-Arabinofuranosylhypoxanthine-3'-phosphate

To an ice cooled solution of 9-$\beta$-D-arabinofuranosyladenine-3'-phosphate (100 mg) in water (1.0 ml) and glacial acetic acid (0.15 ml) was added sodium nitrite (115 mg). The flask was loosely stoppered and stirred overnight at 5°. After evaporation and neutralization with potassium bicarbonate, it was treated in the same way as described in Example IV to yield 80 mg (80%); uv, $\lambda_{max}^{pH\,1}$ 248 nm; $\lambda_{max}^{pH\,7}$ 249 nm; $\lambda_{max}^{pH\,11}$ 252 nm.

The salts of D-arabinofuranosyl purine nucleotides indicated above may be formed in the conventional manner by reaction of the free acid with a base such as NaHCO$_3$ to form, for example, the disodium salt. Reaction with other appropriate bases likewise yield the calcium, barium, potassium and ammonium or substituted ammonium salts, as will be appreciated readily by the art skilled.

EXAMPLE XII

Several compounds of this invention were tested for in vitro activity by the virus rating (VR) method of Sidwell et al, described in Applied Microbiology, 22: 797–801, [1971]. The compound is dissolved in a cell culture medium consisting of vitamins, amino acids, serum, buffer, penicillin, streptomycin and indicator dye in water. The virus suspended in the cell culture medium was added to an established monolayer of Vero, BHK21, HeLa KB or RK 13 cells, and an equal volume of the compound was then added within 15 minutes. The infected treated cells were incubated three days and the degree of viral cytopathogenic effect (CPE) on the cells was graded following microscopic examination. Controls for each experiment included cell controls (cell and cell culture medium only), virus controls (cells and virus and cell culture medium) and toxicity controls (cells and chemical and cell culture medium).

Of the viruses employed in the antiviral experiments, herpes type 1 is implicated in labialis (cold sores), herpes keratitis and herpes encephalitis. The herpes virus is also implicated in infectious mononucleosis. Vaccinia is an avirulent form of smallpox virus employed for smallpox vaccination, which occasionally results in undesired side effects. Myxoma causes death in domestic and wild rabbits, preceded by respiratory illness and severe swelling. Pseudorabies causes infectious bulbar paralysis, also referred to as the "mad itch" disease in cattle, sheep, pigs, dogs and mink.

The results of the in vitro experiments are shown in Table I which follows. The virus rating (VR) system of Sidwell et al described in Applied Microbiology, supra, was used to evaluate the degree of significance of CPE inhibition. A VR greater than 0.5 is indicative of definite antiviral activity, while a VR of less than 0.5 indicates slight antiviral activity.

TABLE I

| Antiviral Activity 9-$\beta$-D-Arabinofuranosyl Purine Nucleotides In Cell Culture Systems | | | |
|---|---|---|---|
| Compound Name | Type 1 Herpes Simplex Virus | Type 2 Herpes Simplex Virus | Vaccinia Virus |
| 9-$\beta$-D-Arabinofuranosyl-hypoxanthine-5'-phosphate* | 0.4–0.9 | 0.6–1.1 | 1.0–1.1 |
| 9-$\beta$-D-Arabinofuranosyl-hypoxanthine-3',5'-cyclic phosphate | 0.7–1.1 | | 0.7 |
| 9-$\beta$-D-Arabinofuranosyl-hypoxanthine-5'-0-methyl-phosphate | 0.4–0.7 | 0.0 | 0.4 |
| 9-$\beta$-D-Arabinofuranosyl-N$^1$-hydroxyhypoxanthine-5'-phosphate | 0.2–0.7 | 0.0–0.6 | 0.1–0.4 |
| 9-$\beta$-D-Arabinofuranosyl-hypoxanthine-3'-phosphate | 1.0 | | |
| 9-B-D-Arabinofuranosyl-adenine-5'-phosphate | 1.3 | | |

The results clearly show that the above compounds exhibit significant in vitro activity against some or all of the listed viruses.

EXAMPLE XIII

The following experiment was carried out using 9-β-D-arabinofuranosylhypoxanthine-5'-phosphate against herpes virus in animals. In this experiment, the compound was dissolved in saline and inoculated intraperitoneally 4 hours after the virus inoculation, continuing twice daily thereafter for 8 days. The results in Table II show that ara-A was less effective and that ara-IMP treatment prevented up to 50% of the mice from dying.

EXAMPLE XV

In this experiment, the compound was evaluated against herpes keratitis in rabbits. Both eyes in New Zealand white rabbits were anesthetized with 0.5% proparacaine HCl and the corneal epithelium was then uniformly scratched. A suspension of type 1 herpes simplex virus was added to each eye in sufficient quantity to cause a uniform keratitis to develop within 3 days. Four animals were treated topically (1 drop per eye) with ara-IMP or ara-A (0.2 or 0.02 M of each) in 1.4% polyvinyl alcohol (PVA), or PVA only in the case of virus controls. Treatment was hourly from 8:00 a.m. to 7:00 p.m., with each drum in Lacrilube ophthal-

TABLE II

Anti-Herpes Encephalitis Activity of 9-β-D-Arabinofuranosyl-hypoxanthine-5'-phosphate Host: 18–20 g Male Swiss Mice  
Virus: Herpes simplex, strain 123  
Virus Dose and Route: 3.2 $LD_{50}$, intracerebral  
Observation Period: 21 days Drug Route: Intraperitoneal  
Treatment started: 4 hr post virus  
Treatment frequency and duration: Twice daily for 8 days post virus

| Name | Dose mg/kg/day | Survivors Total (Toxicity Controls) | Percent Survivor Number Increase | Survivor Increase P* |
|---|---|---|---|---|
| 9-β-D-Arabinofuranosyl-hypoxanthine-5'-phosphate | 500 | 5/5 | 50 | <0.01 |
|  | 250 | — | 40 | <0.05 |
|  | 125 | — | 20 | <0.3 |
|  | 62.5 | — | 10 | >0.3 |
| 9-β-D-Arabinofuranosyl-adenine | 250 | 5/5 | 40 | <0.05 |
|  | 125 | — | 30 | <0.05 |
|  | 62.5 | — | 0 | >0.03 |

*Probability value (chi square analysis).

EXAMPLE XIV

The effect of 9-β-D-arabinofuranosylhypoxanthine-5'-phosphate (ara-IMP) and 9-β-D-arabinofuranosyladenine (ara-A) on herpes encephalitis of mice was tested. In these experiments, young adult Swiss mice were inoculated intracerebrally with a moderately lethal dose (capable of killing ~90–95% of the animals) of type 1 herpes virus. Six hours later the animals were injected intracerebrally with one or more concentrations of either drug in saline solution or with saline only (virus controls). The highest dose used of each drug was the maximum tolerated dose (MTD), i.e., the highest dose not lethally toxic to the animals. The animals were then observed for 21 days and deaths recorded as they occurred. In each experiment, ara-IMP was more effective than ara-A, when the percent increase in survivors (compared to virus control survivors) was plotted against the relative MTD dose of each drug. Up to 5 experiments were run with the various relative drug doses, and the average percent survivor increase was determined.

mic ointment applied at 8:00 p.m. daily for 7 days beginning 24 hours after virus inoculation. The eyes were examined on days 2, 4, 6, and 9 for corneal opacity, lesion size and type, redness, swelling and discharge. A score of 0 (uninfected) to 4 (maximum infection) was given for each. The person examining the eyes did not know which eyes were treated with drug or placebo. The opacity and lesion scores were multiplied by 10 and the other parameter scores were multiplied by 2, then added together for a "weighted lesion score" which was plotted vs day of infection.

EXAMPLE XVI

The effect of ara-IMP and ara-A on equine abortion virus-induced hepatitis mortality in hamsters was tested. Young adult hamsters were inoculated intraperitoneally with a 95% lethal dose of equine abortion virus. Each drug, dissolved or suspended in saline, or saline only for virus controls, was administered intraperitoneally to the animals twice daily for 4 days, beginning 1 hour pre-virus inoculation. The animals were observed 21 days and deaths recorded as they occurred. In each experiment, ara-IMP proved more effective and less toxic than ara-A, keeping up to 100% of the infected animals alive the duration of the study. The results are summarized in Table III.

TABLE III

Effect of 9-β-D-arabinofuranosylhypoxanthine-5'-phosphate (ara-IMP) and 9-β-D-arabinofuranosyladenine (ara-A) on hepatitis associated mortality in hamsters infected with equine abortion virus.

Host: 45–55 g. female Syrian golden hamsters  
Virus Dose: 10 $LD_{50}$ ($10^{-6.8}$)  
Virus Inoculation Route: i.p.

Treatment Route: i.p.  
Treatment Schedule: twice daily for four days starting 1 hr pre-virus inoculation.  
Observation Period: 21 days

| Expt. No. | Treatment | Toxicity Control Surv/Total | Infected, Treated Surv/Total | Survival Increase $p^a$ | Infected, Treated Mean Survival Time$^b$ (days) | Mean Surv. Increase $p^c$ |
|---|---|---|---|---|---|---|
| 1 | Ara-IMP, 250 mg/kg/day | 3/3 | 10/10 | <0.001 | >21 | <0.001 |
|  | Ara-IMP, 125 mg/kg/day | 3/3 | 10/10 | <0.001 | >21 | <0.001 |
|  | Ara-A, 250 mg/kg/day | 2/3 | 0.8 | — | 9.2 | <0.001 |
|  | Ara-A 125 mg/kg/day | 2/2 | 8/9 | <0.001 | 13 | —$^d$ |

TABLE III-continued

Effect of 9-β-D-arabinofuranosylhypoxanthine-5'-phosphate (ara-IMP) and 9-β-D-arabinofuranosyladenine (ara-A) on hepatitis associated mortality in hamsters infected with equine abortion virus.

Host: 45-55 g. female Syrian golden hamsters  
Virus Dose: 10 LD$_{50}$ (10$^{-6.8}$)  
Virus Inoculation  
Route: i.p.

Treatment Route: i.p.  
Treatment Schedule: twice daily for four days starting 1 hr pre-virus inoculation.  
Observation Period: 21 days

| Expt. No. | Treatment | Toxicity Control Surv/Total | Infected, Treated Surv/Total | Survival Increase p$^a$ | Infected, Treated Mean Survival Time$^b$ (days) | Mean Surv. Increase p$^c$ |
|---|---|---|---|---|---|---|
|  | Virus control (saline treatment) |  | 2/20 |  | 4.1 |  |
| 2 | Ara-IMP, 250 mg/kg/day | 3/3 | 10/10 | <0.001 | >21 | <0.001 |
|  | Ara-IMP, 62.5 mg/kg/day | — | 9/10 | <0.001 | 8 | —$^d$ |
|  | Ara-A, 250 mg/kg/day | 2/3 | 3/10 | 0.09 | 12 | <0.001 |
|  | Ara-A, 62.5 mg/kg/day | — | 10/10 | <0.001 | >21 | <0.001 |
|  | Virus control (saline treatment) |  | 1/20 |  | 3.6 |  |

$^a$P = Probability (Fisher's exact test)  
$^b$Animals dying on or before day 21.  
$^c$P = Probability (t test)  
$^d$Insufficient animals died for accurate statistical analysis.

We claim:
1. Compounds of the structure:

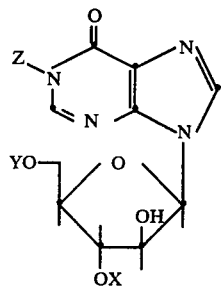

wherein Z is H or hydroxy; and one of X or Y is H and the other is

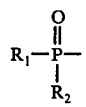

or X and Y together are

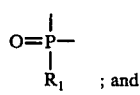

; and

R$_1$ is OH, O—C$_1$—C$_6$-alkyl or OM; and R$_2$ is OH or OM; and M is ammonium, tri-ethyl ammonium, alkali metal, or alkaline earth metal; provided that when X is H, R$_1$ is not OH or OM.

2. Compounds of claim 1 of the strcture:

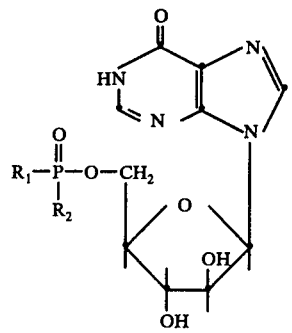

wherein R$_1$ is —O—C$_1$—C$_6$-alkyl and R$_2$ is OH or OM and M is ammonium, tri-ethyl ammonium, alkali metal, or alkaline earth metal.

3. Compounds of claim 1 of the structure:

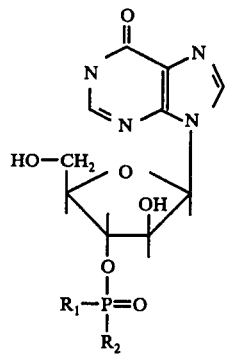

wherein R$_1$ is OH, —O—C$_1$—C$_6$-alkyl or OM and R$_2$ is OH or OM and M is ammonium, tri-ethyl ammonium, alkali metal, or alkaline earth metal.

4. Compounds of claim 1 of the structure:

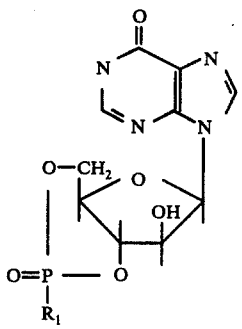

wherein R₁ is OH, —O—C₁—C₆-alkyl or OM and M is ammonium, tri-ethyl ammonium, alkali metal, or alkaline earth metal.

5. 9-β-D-Arabinofuranosylhypoxanthine-3',5'-cyclic phosphate.

6. 9-β-D-Arabinofuranosylhypoxanthine-5'-O-methylphosphate.

7. 9-β-D-Arabinofuranosyl-N¹-hydroxyhypoxanthine-5'-phosphate.

8. 9-β-D-Arabinofuranosylhypoxanthine-3'-phosphate.

9. 9-β-D-Arabinofuranosyladenine-5'-O-methylphosphate.

10. 9-β-D-Arabinofuranosyladenine-3'-phosphate.

11. An antiviral composition for the treatment of DNA virus infections containing as its active ingredient an effective amount of the compound 9-β-D-arabinofuranosylhypoxanthine 5'-phosphate in a pharmaceutical carrier.

12. An antiviral composition for the treatment of DNA virus-caused infections containing as its active ingredient an effective amount of a compound chosen from the group 9-β-D-arabinofuranosylhypoxanthine 5'—O—C₁—C₆ alkyl phosphate, 9-β-D-arabinofuranosylhypoxanthine 3'-phosphate, and 9-β-D-arabinofuranosylhypoxanthine 3',5'-cyclic phosphate in a pharmaceutical carrier.

13. A process of inhibiting the development of DNA virus-caused viral infections in warm-blooded animals comprising administering to said warm-blooded animals a pharmaceutical composition containing as the active component at least about 0.001 percent by weight, based on the total weight of the composition, the compound 9-β-D-arabinofuranosylhypoxanthine 5'-phosphate.

14. A process of inhibiting the development of DNA virus-caused viral infections in warm-blooded animals comprising administering to said warm-blooded animals a pharmaceutical composition containing as the active component at least about 0.001 percent by weight, based on the total weight of the composition, a compound chosen from the group 9-β-D-arabinofuranosylhypoxanthine 5'—O—C₁—C₆ alkyl phosphate, 9-β-D-arabinofuranosylhypoxanthine 3'-phosphate, and 9-β-D-arabinofuranosylhypoxanthine 3',5'-cyclic phosphate.

* * * * *